(12) United States Patent
Chuang et al.

(10) Patent No.: US 7,427,670 B2
(45) Date of Patent: Sep. 23, 2008

(54) CYTOCHROME P450 24 (CYP24) MONOCLONAL ANTIBODY AND METHODS AND USES THEREOF

(75) Inventors: Samuel Suming Chuang, Brampton (CA); Andrew Howard Collop, Toronto (CA)

(73) Assignee: Cytochroma Inc., Markham, Ontario ( * ) Notice: Subject to any disclaimer, the term of this patent is extended or adjusted under 35 U.S.C. 154(b) by 438 days.

(21) Appl. No.: 11/013,435

(22) Filed: Dec. 17, 2004

(65) Prior Publication Data

US 2005/0208055 A1 Sep. 22, 2005

Related U.S. Application Data

(60) Provisional application No. 60/530,604, filed on Dec. 19, 2003.

(51) Int. Cl.
*C07K 16/00* (2006.01)
(52) U.S. Cl. .................... 530/388.1; 435/326
(58) Field of Classification Search ............. None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 2004/0076955 A1* | 4/2004 | Mack et al. | 435/6 |

FOREIGN PATENT DOCUMENTS

| | | |
|---|---|---|
| EP | 171496 | 2/1986 |
| EP | 0173494 | 3/1986 |
| EP | 0239400 | 9/1987 |
| GB | 2177096 B | 9/1985 |
| WO | WO 92/06193 | 4/1992 |
| WO | WO 97/49815 | 12/1997 |
| WO | WO 01/44443 | 6/2001 |

OTHER PUBLICATIONS

Ngo et al., 1994, The Protein Folding Problem and Tertiary Structure Prediction, pp. 492-495.*
Attwood, Science 2000; 290:471-473.*
Skolnick et al., Trends in Biotech. 2000; 18(1):34-39.*
Metzler et al. ,Nature Structural Biol. 1997; 4:527-531.*
Chagnaud et al., Brain Research, 1989, vol. 481(1):175-180.*
Gavilondo et al. BioTechquitees, vol. 29, p. 128-145, 2000.*
White et. al., Identification of the Retinoic Acid-inducible All-trans-retinoic Acid 4-Hydroxylase, Journal of Biological Chemistry, vol. 271, No. 47, Nov. 22, 1996, pp. 29922-29927.

Jones et al., Expression and Activity of Vitamin D-Metabolizing Cytochrome P450s (CYP1α and CYP24) in Human Nonsmall Cell Lung Carcinomas, Journal of Endocrinology, vol. 140, No. 7, July, pp. 3303-3310.
Dilworth et. al., Different Mechanisms of Hydroxylation Site Selection by Liver and Kidney Cytochrome P450 Species (CYP27 and CYP24) Involved in Vitamin D Metabolism, Journal of Biological Chemistry, vol. 270, No. 28, Jul. 14, 1995, pp. 16766-16774.
Chen et. al., Isolation and expression of human 1,25-dihydroxyvitamin D3 24-hydroxylase cDNA, Proc. Natl. Acad. Sci., vol. 90, May 1993, pp. 4543-4547.
Yoshimura et. al., Molecular cloning of 25-hydroxyvitamin D-3 24-hydroxylase (Cyp-24) from mouse kidney: its inducibility by vitamin D-3, Biochemica et Biophysica Acta, Oct. 17, 1995, 1264(1), pp. 26-28.
Kohler et. al., Continuous cultures of fused cells secreting antibody of predefined specificity, Nature, 256(5517), 1975, pp. 495-497.
Kozbor et. al., The production of monoclonal antibodies from human lymphocytes, Immunology Today, vol. 4,No. 3, 1983, pp. 72-79.
Cole et. al., The EBV-Hybridoma Technique and its Application to Human Lung Cancer, Monoclonal Antibodies and Cancer Therapy, Allen R. Bliss, 1985, pp. 77-96.
Huse et. al., Generation of a Large Combinatorial Library of the Immunoglobulin Repertorie in Phage Lambda, Science, 246, Dec. 8, 1989, pp. 1275-1281.
Morrison et. al., Chimeric human antibody molecules: Mouse antigen-binding domains with human constant region domains, Proc. Natl. Acad. Sci., vol. 81, Nov. 1984, pp. 6851-6855.
Takeda et. al., Construction of chimaeric processed immunoglobulin genes containing mouse variable and human constant region sequences, Nature, vol. 314, Apr. 1985, pp. 452-454.
Teng et. al., Construction and testing of mouse-human heteromyelomas for human monoclonal antibody production, Proc. Natl. Acad, Sci., vol. 80, Dec. 1983, pp. 7308-7312.
Olsson et. al., Human-Human Monoclonal Antibody-Producing Hybridomas: Technical Aspects, Methods in Enzymology, vol. 92, Academic Press Inc., 1983, pp. 3-16.
Ward et. al., Binding activities of a repertoire of single immunoglobulin variable domains secreted from *Escherichia coli*, Nature, vol. 341, Oct. 12, 1989, pp. 544-546.
McCafferty et. al., Phage antibodies: filamentous phage displaying antibody variable domains, Nature, vol. 348, Dec. 6, 1990, pp. 552-554.

* cited by examiner

*Primary Examiner*—Eileen B. O'Hara
*Assistant Examiner*—Yunsoo Kim
(74) *Attorney, Agent, or Firm*—Marshall, Gerstein & Borun LLP

(57) ABSTRACT

This invention relates to a monoclonal antibody for CYP24 and to methods and uses therefore, such as in Western blot analysis, immunohistochemisty, protein purification; diagnostics, such as for cancer, vitamin D metabolic conditions and the like.

3 Claims, 2 Drawing Sheets

FIGURE 1

```
  1    msspisksrs  laaflqqlrs  prqpprlvts  taytspqpre
 41    vpvcpltagg  etqnaaalpg  ptswpllgsl  lqilwkgglk
 81    kqhdtlveyh  kkygkifrmk  lgsfesvhlg  spcllealyr
121    tesaypqrle  ikpwkayrdy  rkegygllil  egedwqrvrs
161    afqkklmkpg  evmkldnkin  evladfmgri  delcderghv
201    edlyselnkw  sfesiclvly  ekrfgllqkn  agdeavnfim
241    aiktmmstfg  rmmvtpvelh  kslntkvwqd  htlawdtifk
281    svkacidnrl  ekysqqpsad  flcdiyhqnr  lskkelyaav
321    telqlaavet  tanslmwily  nlsrnpqvqq  kllkeiqsvl
361    penqvpraed  lrnmpylkac  lkesmrltps  vpfttrtldk
401    atvlgeyalp  kgtvlmlntq  vlgssednfe  dssqfrperw
441    lqekekinpf  ahlpfgvgkr  mcigrrlael  qlhlalcwiv
481    rkydiqatdn  epvemlhsgt  lvpsrelpia  fcqr
```

FIGURE 2

SEQUENCE LISTING

<160> NUMBER OF SEQ ID NOS: 2

<210> SEQ ID NO 1
<211> LENGTH: 514
<212> TYPE: PRT
<213> ORGANISM: Homo sapiens

<400> SEQUENCE: 1

```
Met Ser Ser Pro Ile Ser Lys Ser Arg Ser Leu Ala Ala Phe Leu Gln
1               5                   10                  15

Gln Leu Arg Ser Pro Arg Gln Pro Pro Arg Leu Val Thr Ser Thr Ala
            20                  25                  30

Tyr Thr Ser Pro Gln Pro Arg Glu Val Pro Val Cys Pro Leu Thr Ala
        35                  40                  45

Gly Gly Glu Thr Gln Asn Ala Ala Ala Leu Pro Gly Pro Thr Ser Trp
    50                  55                  60

Pro Leu Leu Gly Ser Leu Leu Gln Ile Leu Trp Lys Gly Gly Leu Lys
65                  70                  75                  80

Lys Gln His Asp Thr Leu Val Glu Tyr His Lys Tyr Gly Lys Ile
                85                  90                  95

Phe Arg Met Lys Leu Gly Ser Phe Glu Ser Val His Leu Gly Ser Pro
            100                 105                 110

Cys Leu Leu Glu Ala Leu Tyr Arg Thr Glu Ser Ala Tyr Pro Gln Arg
        115                 120                 125

Leu Glu Ile Lys Pro Trp Lys Ala Tyr Arg Asp Tyr Arg Lys Glu Gly
    130                 135                 140

Tyr Gly Leu Leu Ile Leu Glu Gly Glu Asp Trp Gln Arg Val Arg Ser
145                 150                 155                 160

Ala Phe Gln Lys Lys Leu Met Lys Pro Gly Glu Val Met Lys Leu Asp
            165                 170                 175

Asn Lys Ile Asn Glu Val Leu Ala Asp Phe Met Gly Arg Ile Asp Glu
        180                 185                 190

Leu Cys Asp Glu Arg Gly His Val Glu Asp Leu Tyr Ser Glu Leu Asn
    195                 200                 205

Lys Trp Ser Phe Glu Ser Ile Cys Leu Val Leu Tyr Glu Lys Arg Phe
210                 215                 220

Gly Leu Leu Gln Lys Asn Ala Gly Asp Glu Ala Val Asn Phe Ile Met
225                 230                 235                 240

Ala Ile Lys Thr Met Met Ser Thr Phe Gly Arg Met Met Val Thr Pro
            245                 250                 255

Val Glu Leu His Lys Ser Leu Asn Thr Lys Val Trp Gln Asp His Thr
        260                 265                 270

Leu Ala Trp Asp Thr Ile Phe Lys Ser Val Lys Ala Cys Ile Asp Asn
    275                 280                 285

Arg Leu Glu Lys Tyr Ser Gln Gln Pro Ser Ala Asp Phe Leu Cys Asp
290                 295                 300

Ile Tyr His Gln Asn Arg Leu Ser Lys Lys Glu Leu Tyr Ala Ala Val
305                 310                 315                 320

Thr Glu Leu Gln Leu Ala Ala Val Glu Thr Thr Ala Asn Ser Leu Met
            325                 330                 335

Trp Ile Leu Tyr Asn Leu Ser Arg Asn Pro Gln Val Gln Gln Lys Leu
        340                 345                 350

Leu Lys Glu Ile Gln Ser Val Leu Pro Glu Asn Gln Val Pro Arg Ala
    355                 360                 365

Glu Asp Leu Arg Asn Met Pro Tyr Leu Lys Ala Cys Leu Lys Glu Ser
370                 375                 380

Met Arg Leu Thr Pro Ser Val Pro Phe Thr Thr Arg Thr Leu Asp Lys
385                 390                 395                 400

Ala Thr Val Leu Gly Glu Tyr Ala Leu Pro Lys Gly Thr Val Leu Met
            405                 410                 415
```

```
                                -continued

Leu Asn Thr Gln Val Leu Gly Ser Ser Glu Asp Asn Phe Glu Asp Ser
            420                 425                 430

Ser Gln Phe Arg Pro Glu Arg Trp Leu Gln Glu Lys Glu Lys Ile Asn
        435                 440                 445

Pro Phe Ala His Leu Pro Phe Gly Val Gly Lys Arg Met Cys Ile Gly
    450                 455                 460

Arg Arg Leu Ala Glu Leu Gln Leu His Leu Ala Leu Cys Trp Ile Val
465                 470                 475                 480

Arg Lys Tyr Asp Ile Gln Ala Thr Asp Asn Glu Pro Val Glu Met Leu
                485                 490                 495

His Ser Gly Thr Leu Val Pro Ser Arg Glu Leu Pro Ile Ala Phe Cys
            500                 505                 510

Gln Arg

<210> SEQ ID NO 2
<211> LENGTH: 17
<212> TYPE: PRT
<213> ORGANISM: Homo sapiens

<400> SEQUENCE: 2

Gln Arg Leu Glu Ile Lys Pro Trp Lys Ala Tyr Arg Asp Tyr Arg Lys
1               5                   10                  15

Glu
```

CYTOCHROME P450 24 (CYP24) MONOCLONAL ANTIBODY AND METHODS AND USES THEREOF

PRIORITY APPLICATIONS

This application claims the right of priority from previously filed U.S. provisional patent application No. 60/530,604 entitled "Cytochrome P450 24 (CYP24) Monoclonal Antibody and Methods and Uses Thereof" filed Dec. 19, 2003, all of which is herein incorporated by reference.

FIELD OF THE INVENTION

The invention relates to CYP24 monoclonal antibodies and methods and uses thereof. It also relates to kits comprising said monoclonal antibody.

BACKGROUND OF THE INVENTION

The cytochrome P450s comprise a large gene superfamily that encodes over 500 distinct heme-thiolate proteins that catalyze the oxidation of drugs and numerous other compounds in the body. It is of considerable interest in the pharmaceutical and other fields to identify cytochrome P450s and the role they play in the metabolism of individual compounds. Cytochrome P450s are heme-containing enzymes that strongly absorb at a wavelength of 450 nm when the heme is bound to a molecule of carbon monoxide. They are most well known for their ability to catalyze the metabolism of a wide variety of drugs, xenobiotics, carcinogens, mutagens and pesticides, and they are also involved in catalyzing reactions that make or degrade cholesterol, steroids, and other lipids. The reactions performed by these enzymes are generally oxidations, hydroxylations, acetylations, and demethylations. Mutations in cytochrome P450s or abnormal expression levels can cause a number of human diseases such as glaucoma and breast cancer. Cytochrome P450s are also involved in the metabolism of a number of vitamins, such as Vitamin A (retinoic acid) [White et. al. (1996) J. Biol. Chem. Nov. 22: 271(47): 29922-7; WO197/49815; WO 01/44443] and Vitamin D [Jones, G. et. al. (1999) July; 140(7):3303-10; Dilworth F J, et. al. (1995) July 14; 270(28); 16766-74. In particular, cytochrome P450s, CYP27A, CYP27B and CYP24, are involved in Vitamin $D_3$ metabolism. Vitamin $D_3$, a secosteroid, is metabolized into its active form by CYP27A and CYP27B and is then further metabolized by CYP24. CYP24 is a mitochrondrial cytochrome P450 that has previously been characterized. For example, isolated human CYP24 was published in Chen et al. (Isolation and expression of human 1,25-dihydroxyvitamin D3 24-hydroxylase cDNA. Proc Natl Acad Sci USA 1993 May 15;90(10):4543-7). In Chen et al. it was reported that the human 24-hydroxylase 1539 base pair open reading frame encoded a 513 amino acid sequence, 90% homologous to rat Cyp24. Mouse Cyp24 was characterized in Yoshimura et al. (Molecular cloning of 25-hydroxyvitamin D-3 24-hydroxylase (Cyp-24) from mouse kidney: its inducibility by vitamin D-3. Biochim Biophys Acta 1995 Oct. 17; 1264(1):26-8).

The vitamin D metabolic pathway is part of a vital endocrine system that is highly regulated at certain stages and produces metabolites that control the secretion of the parathyroid gland hormones. $1\alpha,25(OH)_2D_3$, a hormone produced in the vitamin D pathway, regulates phosphate and calcium levels in the blood which in turn control bone mass, the state of bones, and affect cellular differentiation in the skin and the immune system. In the vitamin D pathway, cytochrome P450s introduce functional groups by hydroxylation usually at positions 1, 25, and 24 of the steroid.

The metabolism of vitamin D begins with 25-hydroxylation of vitamin $D_3$ or $D_2$ in the liver to $25(OH)D_3$. $25(OH)D_3$ and a second metabolite, $1\alpha,25(OH)_2D_3$, are converted to $24,25(OH)_2D_3$ and $1,24,25(OH)_3D_3$ by CYP24, a mitochondrial P450 involved in the vitamin D pathway, respectively. CYP24 expression is induced by $1,25(OH)_2D_3$ and is found in the kidney as well as other vitamin D target tissues such as the parathyroid cells, keratinocytes, osteoblasts, and enteroctyes.

There are a number of vitamin D related medical conditions. More information on vitamin D conditions can be found in the Proceedings of the Workshop on Vitamin D (Walter de Gruyter publishing, Berlin), proceedings 1 to 11. For instance, vitamin D deficiency has been related to the following:

1. in the parathyroid—hyper- and hypo-parathyroidism, pseudohypo-parathyroidism, secondary hyperparathyroidism;
2. in the pancreas—diabetes;
3. in the thyroid—medullary carcinoma;
4. in the skin—psoriasis;
5. in the lung—sarcoidosis and tuberculosis;
6. in the kidney—chronic renal disease, glomerulonephritis, IgA nephropathy, membraneous nephropathy, glomerulosclerosis, nephrosis, renal insufficiency, hypophosphtatemic VDRR, vitamin D dependent rickets;
7. in the bone—anticonvulsant treatment, fibrogenisis imperfecta ossium, osteitits fibrosa cystica, osteomalacia, hypocalcemia, osteoporosis, osteopenia, osteosclerosis, renal osteodytrophy, rickets;
8. in the intestine—glucocorticoid antagonism, idopathic hypercalcemia, malabsorption syndrome, steatorrhea, tropical sprue;
9. in the prostate—cancer; and
10. in the breast—cancer.

More common conditions related to vitamin D or vitamin D metabolite deficiency are obesity problems, hyperphosphatemic tumoral calcinosis, sarcoidosis, tuberculosis, primary hyperparathyroidism, vitamin D dependent rickets type 11, cholestatic or paremchymal liver disease.

Since CYP24 is involved in maintaining vitamin D homeostasis and is implicated in the development of these diseases, it is important to understand how CYP24 activity is and can be modulated in vivo and in vitro. There is also a need for drug design and drug screening methods to identify substances that modulate CYP24.

SUMMARY OF THE INVENTION

The present inventors have made and isolated a monoclonal antibody for CYP24. In one embodiment, the monoclonal antibody is particular to the epitope from human CYP24 peptide positions 127-143 (accession #19862747).

In one embodiment the epitope is C-QRLEIKP-WKAYRDYRKE-NH$_2$ (SEQ. ID. No. 2). Blast searches reveal that the antibody may cross-react with rat, mouse, pig and chicken Cyp24.

The invention also provides hybridomas that can be used to prepare the monoclonal antibody of the invention.

The antibody of the invention can take on many forms. It can be used as is, it can be purified and/or isolated, it can be tagged to various conjugates such as biotin, avidin, fluorochromes, and horseradish peroxidase (HRP). It can also be fragmented into F(ab)$_2$ or ab fragments. In another aspect, the antibody of the invention can be humanized.

In another embodiment, the invention provides for methods and uses for the monoclonal antibody, such as a molecular biology tool, use in Western blot analysis, immunohistochemisty, protein purification, Enzyme-Linked Immunosorbent Assay (ELISA), radioimmunoassay (RIA), immunopurification; or as a diagnostic tool, such as for cancer and vitamin D metabolic related disorders.

The monoclonal antibody could also be used to screen for substances, such as drugs and compounds that bind CYP24 and/or can modulate CYP24 expression and/or activity.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

"Obvious chemical equivalent" as used herein means a compound (e.g. nucleic acid molecule, peptide, antibody or portion thereof or other compound) or a method of making a monoclonal antibody that has no material effect on the way that the invention works. The fact that the variant has no material effect will be obvious to a reader skilled in the art. Examples of obvious chemical equivalents include but are not limited to obvious variations of CYP24 or epitope of CYP24 or monoclonal antibody of CYP24, degenerate CYP24 or CYP24 epitope or CYP24 monoclonal antibody coding nucleic acid sequences, vectors comprising said sequences or reagents and conservative amino acid substitutions of CYP24 or CYP24 epitope or CYP24 monoclonal antibody.

"Modulator" as used herein means any substance (e.g. drug, chemical, peptide, antibody, nucleic acid molecule) or condition (temperature, salt levels, pH, etc.) that can increase, decrease or maintain (e.g. homeostasis—increase or decrease as required) CYP24 expression or activity. These can include any agonist, antagonist or simulator.

"CYP24" as used herein means an amino acid sequence from a family of cytochrome P450's that catalyses the following reaction: Vitamin D metabolites—$25(OH)D_3$ and $1\alpha,25(OH)_2D_3$, to $24,25(OH)_2D_3$ and $1,24,25(OH)_3D_3$, respectively. As used herein, "CYP24" or "CYP24 peptide", "CYP24 polypeptide" or "CYP24 protein" are used interchangeably. "CYP24" has the amino acid sequence as shown in SEQ. ID. NO. 1 or that of a homolog, a species homolog, analog, or derivative of SEQ. ID. NO. 1 that has the above-noted enzymatic activity. "CYP24" also includes a biologically active fragment or obvious chemical equivalent of SEQ. ID. NO. 1, homolog, species homolog, analog or derivative thereof.

CYP24 polypeptide may include various structural forms of the primary protein that retain biological activity. For example, a polypeptide of the invention may be in the form of acidic or basic salts or in neutral form. The CYP24 polypeptides may be modified by either natural processes, such as post-translational processing or by chemical modification techniques, which are well known in the art. Such modifications are described in basic texts, research manuals and research literature. Modifications may occur anywhere in the CYP24 including the peptide backbone, the amino acid sidechain and the amino or carboxyl termini. It will be appreciated that the same type of modification may be present in the same or varying degree at several sites in a given CYP24 polypeptide. In addition, a given CYP24 may contain many types of modification. The modifications may result from post-translational natural processes or may be made by synthetic methods.

The term "analog" includes any polypeptide such as CYP24 having an amino acid residue sequence substantially identical to the CYP24 sequences described in this application in which one or more residues have been conservatively substituted with a functionally similar residue and which displays CYP24 activity as described herein. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" refers to a polypeptide such as CYP24 derivative having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5 hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

Suitable regions of CYP24 (epitopes) to be used as an antigen to generate CYP24 specific antibodies were identified by running the amino acid sequence through standard computer programs (eg. OMIGA.RTM. [2.0]) to predict antigenicity, hydrophilicity (Kyte-Doolittle method), surface probability, and secondary amino acid structure (Chou Fasman method). Regions of CYP24 that were predicted to be highly antigenic, highly hydrophilic, located on the surface of the protein, and form part of a helix structure were then analyzed using the BLAST P search engine for sequence uniqueness. Based on these criteria, the peptide region 127-143 (SEQ. ID.

NO. 2) of CYP24 (SEQ. ID. NO. 1) was selected to be used for monoclonal antibody production. The use of the epitope to make monoclonal antibodies of the invention is also encompassed within the scope of this invention, as well as the method of making CYP24 monoclonal antibodies using the epitope SEQ. ID. NO. 2.

Nucleic acids encoding the epitope of the invention (SEQ. ID. NO. 2), or derivatives or functional equivalents thereof are also provided in the present invention. Conventional methods can be used to prepare the antibodies of the invention. For example, by using a peptide of CYP24, polyclonal antisera or monoclonal antibodies can be made using standard methods. A suitable host, (e.g., a mouse, rat, hamster, rabbit, goat, or chicken) can be immunized with an immunogenic form of the peptide which elicits an antibody response in the host. Techniques for conferring immunogenicity on a peptide include conjugation to carriers (e.g BSA) or other techniques well known in the art. For example, the protein or peptide can be administered in the presence of an adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (splenocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for CYP24 as described herein.

The term "antibody" as used herein is intended to include fragments thereof which also specifically react with CYP24, or peptide thereof, having the activity of the CYP24 or epitope of CYP24. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of CYP24 antigens of the invention (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with CYP24 of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against CYP24 proteins may also be generated by screening expression libraries encoding immunoglobulin genes, or portions thereof, expressed in bacteria with peptides produced from the nucleic acid molecules of CYP24. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a CYP24 "humouse", for example the model developed by Genpharm, can be used to produce antibodies or fragments thereof.

Kits of the Invention

The monoclonal antibody can be placed into a kit for conducting the assays and screening tools of the invention. The kits can comprise a sample of monoclonal antibody and optional directions for its use and applications.

Methods and Assays Using the Monoclonal Antibody of the Invention

The monoclonal antibody of the present invention can be used to isolate or harvest CYP24 by exposing a sample (e.g. a mitochondrial preparation of a CYP24 expressing cell line) or a cell line that stably expresses CYP24, or other sample that has CYP24 with the monoclonal antibody under conditions that promote binding of CYP24 with the antibody; and isolating the CYP24/monoclonal antibody complex. The method can further comprise recovering the CYP24 from the complex by exposing the complex to conditions to promote dissociation of the complex and then recovering the CYP24 thereafter using techniques known in the art. In one embodiment, the monoclonal antibody can be bound to a support (e.g. solid stationary support as in a column) and the CYP24 containing sample can be run by the support under conditions that promote CYP24/monoclonal antibody complex formation. A buffer promoting dissociation of the complex can then be used to wash and recover the CYP24 from the monocolonal antibody/support.

The monoclonal antibody of the present invention can be used to monitor CYP24 expression and levels thereof and activity in the presence or absence of other substances (potential CYP24 modulators) using techniques known in the art, such as immunoblotting, ELISAs, radioimmunoassays, etc. (e.g., Harlow and Lane. Antibodies: A Laboratory Manual (1988) Cold Spring Harbor Laboratory). In these embodiments, the monoclonal antibody may be labeled to promote detection of any resulting CYP24/monoclonal antibody complex or lack thereof. For instance the monoclonal antibody can be radiolabeled, enzyme-linked, or fluorescently labeled.

Other labels are known in the art. This can also promote CYP24 titer determination (e.g. quantification). Levels of CYP24 (quantitative or qualitative) can be used to assess CYP24 expression and activity and effect of modulators on said expression and/or activity, using techniques known in the art such as western blot (Harlow and Lane. Antibodies: A Laboratory Manual (1988) Cold Spring Harbor Laboratory CYP24 expressing cell lines, such as the Human Epidermal Keratinocyte (HEK) cell line or a stable CYP24 expressing cell line can be used in the screening assays of the invention, such as in the modulator screening assays. Potential modulators may include but are not limited to anti-sense CYP24 nucleic acids, and analogs or derivatives of vitamin D. Ketoconazole is also a known inhibitor of CYP24.

Assays can include incubating CYP24 or CYP24 expressing cells with known substrates in the presence of a potential modulator and then assessing the resultant activity of the modulator on CYP24 activity and/or expression using monoclonal antibody assessment techniques.

In one embodiment, the invention provides a method of identifying a modulator of a CYP24 polypeptide comprising,
(i) culturing a CYP24 expressing cell line under conditions wherein the cell expresses the CYP24 in the presence of a CYP24 substrate and a candidate modulator, under conditions, for instance that permit CYP24/substrate activity; and
(ii) determining whether the candidate modulator modulates CYP24/substrate activity, wherein increased or decreased CYP24 expression indicates that the candidate modulator is a modulator of the CYP24 polypeptide. In one embodiment, the activity is monitored using the CYP24 monoclonal antibody of the invention. In another embodiment, the activity is monitored by one or more of the following:
  a. monitoring binding of CYP24 with the candidate modulator using monoclonal antibody of the invention; and/or
  b. monitoring CYP24 gene expression using monoclonal antibody of the invention;

In another embodiment the affect of the candidate modulator is determined by comparing the affect of said candidate modulator with that of a control. In one embodiment the control comprises conducting the assay in the absence of the candidate modulator and/or in the presence of a known modulator with known effects on CYP24. In yet another embodiment the step of determining whether the candidate compound modulates CYP24 polypeptide activity comprises adding a substrate to the cell and detecting increased or decreased activity of the CYP24 on the substrate in the presence of the candidate compound.

The following non-limiting examples are illustrative of the present invention:

EXAMPLES

Example 1

Manufacture of CYP24 Monoclonal Antibody and Hybridomas Producing Same

The peptide C-QRLEIKPWKAYRDYRKE-NH2, (SEQ. ID. NO. 2) which relates to human CYP24 peptide positions 127-143 (accession #19862747) (SEQ. ID. NO. 1) was obtained (AnaSpec, Inc.) and the following general protocol was used to produce the CYP24 monoclonal antibody.

Materials:
Peptide immunogen conjugated to carrier protein (i.e. bovine serum albumin [BSA] or Keyhole Limpet Hemocyanin [KLH])
Complete Freund's adjuvant
20 gauge needle
1 ml syringe
6 Balb/C mice
SP2/0 cells
100×OPI media (1.5 g oxaloacetate, 500 mg sodium pyruvate, 2000 IU bovine insulin, in 100 ml $H_2O$)
Dulbecco's modified Eagle's (DME) media
100×AH (Add 0.136 g hypoxanthine in $H_2O$, heat to 70° C. to dissolve, add 10 mg azaserine)
100×H (Add 0.136 g hypoxanthine in $H_2O$, heat to 70° C. to dissolve) 96-well microtiter plates
Polyethylene glycol 1500 (PEG) (before use, pre-warm 0.3 g in 50° C. Once melted, add 0.7 ml medium without serum and transfer to 37° C. water bath)

Method

First, 6 Balb/c mice were immunized at Day 1 with C-QR-LEIKPWKAYRDYRKE-$NH_2$ (SEQ. ID. No. 2) conjugated to KLH (10-200 μg) mixed in complete Freund's adjuvant (0.3-0.5 ml) into suspension. The mice were either injected intraperitonelly with 0.5 or subcutaneously with 0.3 ml of the suspension. After 21-28 days after the initial immunization, a subsequent "booster" injection was administered to the mice, comprising 10-200 μg of C-QRLEIKPWKAYRDYRKE-$NH_2$ (SEQ. ID. No. 2) conjugated to KLH intraperitonelly with 0.5 or subcutaneously with 0.3 ml of incomplete Freund's adjuvant. At 21-28 days after the booster shot, a second identical booster shot was administered. At 21-28 days after the second booster, a test bleed from the mice was taken and an ELISA test of the sera against the immunogen, C-QR-LEIKPWKAYRDYRKE-$NH_2$ (SEQ. ID. No. 2) conjugated to BSA was performed for titering. The best reacting mouse (or mice) was selected for fusion and hybridoma development.

Spleen cells from the best reacting mice were then fused with an immortalized mouse myeloma cell line by first obtaining the spleen cells by euthanizing the mice and removing their spleens in aseptic conditions. Single spleen cells were then isolated in DME medium. The isolated spleen cells and myeloma cells, that were prepared one week before use by growing SP120 myeloma cells in 2×OPI media and 10% serum containing azaserine, were washed separately, in pre-warmed DME media without serum and spun down. Each of the cell pellets were resuspended in DME medium without serum. The two cell suspensions were then combined and mixed. The mixture was centrifuged for 5 min at 400 g and all media was carefully removed. 0.2 ml of PEG solution was added and the cells lightly resuspended. The suspension was again centrifuged for 5 min at 400 g. The supernatant was then aspirated. 5 ml of DME medium with 20% serum was then added. The cells were mixed and then centrifuged for another 5 min at 400 g after which all media was carefully removed. The cells were then resuspended in 10 ml of DME medium with 20% serum, 1×OPI, and 1×AH.

The resulting fused hybridomas were then screened by plating the fused hybridomas. 100 μl of cells were added to wells of 20 96-well microtiter plates and placed in a $CO_2$ incubator. Successfully fused hybridoma clones were visible by day 4. The fused cell clones were then screened by ELISA to select positive antibody-secreting parental clones. The potential parental clones were then cloned by "limiting dilution". Isolated clones were screened again by ELISA for the presence of antigen-specific antibodies. The hybridomas comprising antigen-specific antibodies were selected and used for further testing and as a source of CYP24 specific antibody.

Example 2

Monoclonal Antibody Binding with CYP24 and the Effect of CYP24 Protein Expression in HEK Cells Treated with CYP24 Inhibitors HEK Cell Time Course Materials:
  Human Epidermal Keratinocyte Cells (HEK) cells (CYP24 expressing cells)
  Keratinocyte Growth Medium (KGM®; Cambrex)
  HEK Cell Lysis Buffer (0.5 M Tris, pH 6.8, 10% SDS, glycerol, $dH_2O$, protease inhibitor)
  1.7 ml eppendorf tubes
  Isopropanol
  Enhanced Chemiluminescense (ECL) Western Blotting Detection Reagants (Amersham Pharmacia)
  10 nM Calcitriol (Vitamin D)
  10 nM CTAX (Cytochroma Inc.) ("Vitamin D analog")
  10 nM CTAY (Cytochroma Inc.) ("Vitamin D analog")
  10 nM CTAZ (Cytochroma Inc.) ("Vitamin D analog")
  6-well plates (i) HEK Cell Preparation Method:

125 thousand HEK cells per well were placed in 2.5 ml KGM® (2 plates) and incubated overnight @ 37° C. in 5% $CO_2$. After 24 hours, old KGM® was replaced with fresh 2.5 ml KGM®. For 48 hour samples (Plate 1): 2.5 µl isopropanol was added to 1 well; 2.5 µl 10 µM calcitriol was added to 1 well; 2.5 µl 10 µM CTAX was added to 1 well; 2.5 µl 10 µM CTAY was added to 1 well; 2.5 µl 10M CTAZ was added to 1 well. For 24 hour samples (Plate 2): After 24 hours 2.5 µl isopropanol was added to 1 well; 2.5 µl 10M calcitriol was added to 1 well; 2.5 µl 10 µM CTAX was added to 1 well; 2.5 µl 10 µM CTAY was added to 1 well; 2.5 µl 10 µM CTAZ was added to 1 well. After 24 hours, protein was collected by aspirating KGM® from all wells; 250 µl Cell Lysis Buffer was added; lysate was transferred to 1.7 ml eppendorf tube and stored @-20° C. until use.

(ii) Western Blot Method:

The protein samples were subjected to immunoblotting by running them on an SDS page gel, blotting the gel onto nitrocellulose and then screening for the presence of CYP24 using the monoclonal antibody of the invention.

The nitrocellulose strips were incubated with the 10 antibody (Monoclonal antibody of the invention), diluted 1:200 in 1×PBST+2% BSA, O/N at RT, while shaking the 10 antibody was drained and the nitrocellulose was washed 2 times with 1×PBST+2% BSA for 5 min each. The strips were then washed and incubated with the 20 antibody (Mouse Ig-Horseradish Peroxidase-linked whole antibody; Amersham Pharmacia), diluted 1:20,000 with 1×PBST+2% BSA, for 2 hours at RT while shaking. The 2° antibody was then drained and the strips washed 3 times with 1×PBST+2% BSA for 5 min each. The strips were then prepared for ECL detection using techniques known in the art.

The bands developed on the film were compared with the bands from the ladder. P450s are ~55 kDa, therefore they should be just below the 60 kDa marker, which they were.

(d) Densitometric Analysis of CYP24 Western Blot on HEK Cell Lysates

Scion Software was used to analyse pixels of each band. Microsoft Excel was used to subtract control away from each treated sample. Control value was set to 1. The resulting number for treated samples were the relative increase in the amount of protein compared to the control. Results are shown in FIG. 2.

Results

The effect of CYP24 protein expression in HEK cells treated with CYP24 inhibitors was investigated. The results are shown in FIG. 2. HEK cells were incubated with 10 nM of calcitriol (C), CYP24 inhibitors CTAX, CTAY, CTAZ, or alone (O). After 24 or 48 h, cells were collected and lysed with lysis buffer. Cell lysates were then analyzed for CYP24 protein by Western blot analysis using anti-CYP24 mAb as the primary antibody. The results are shown in FIG. 2A. Densitometric analysis of the CYP24 western blot on HEK cells using Scion Software is shown in FIG. 2B. Each sample was expressed as a relative amount of CYP24 protein compared to the control (control=1 unit).

Figure 1:
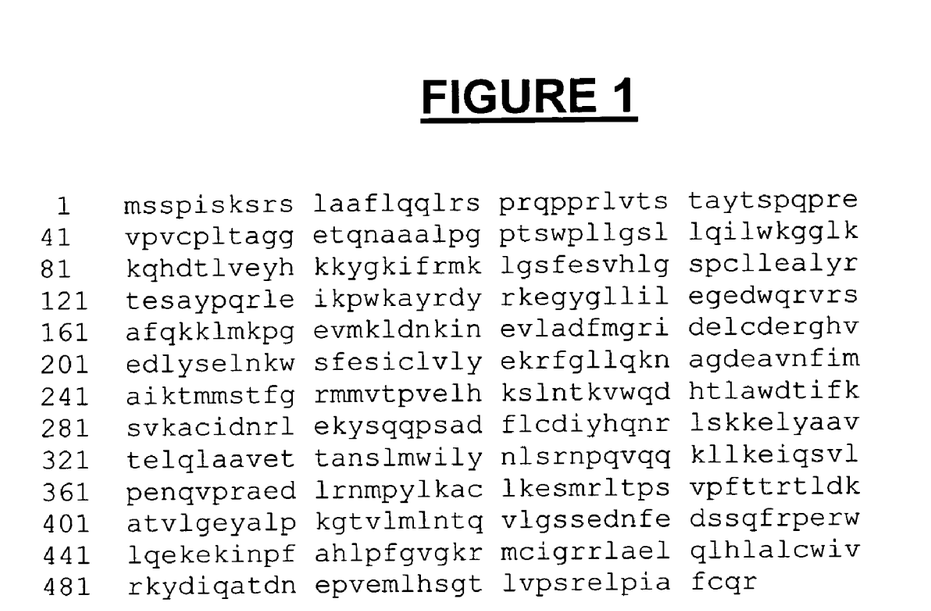
FIG. 1 is the amino acid sequence of CYP24 (SEQ. ID. NO. 1)
Figure 2:
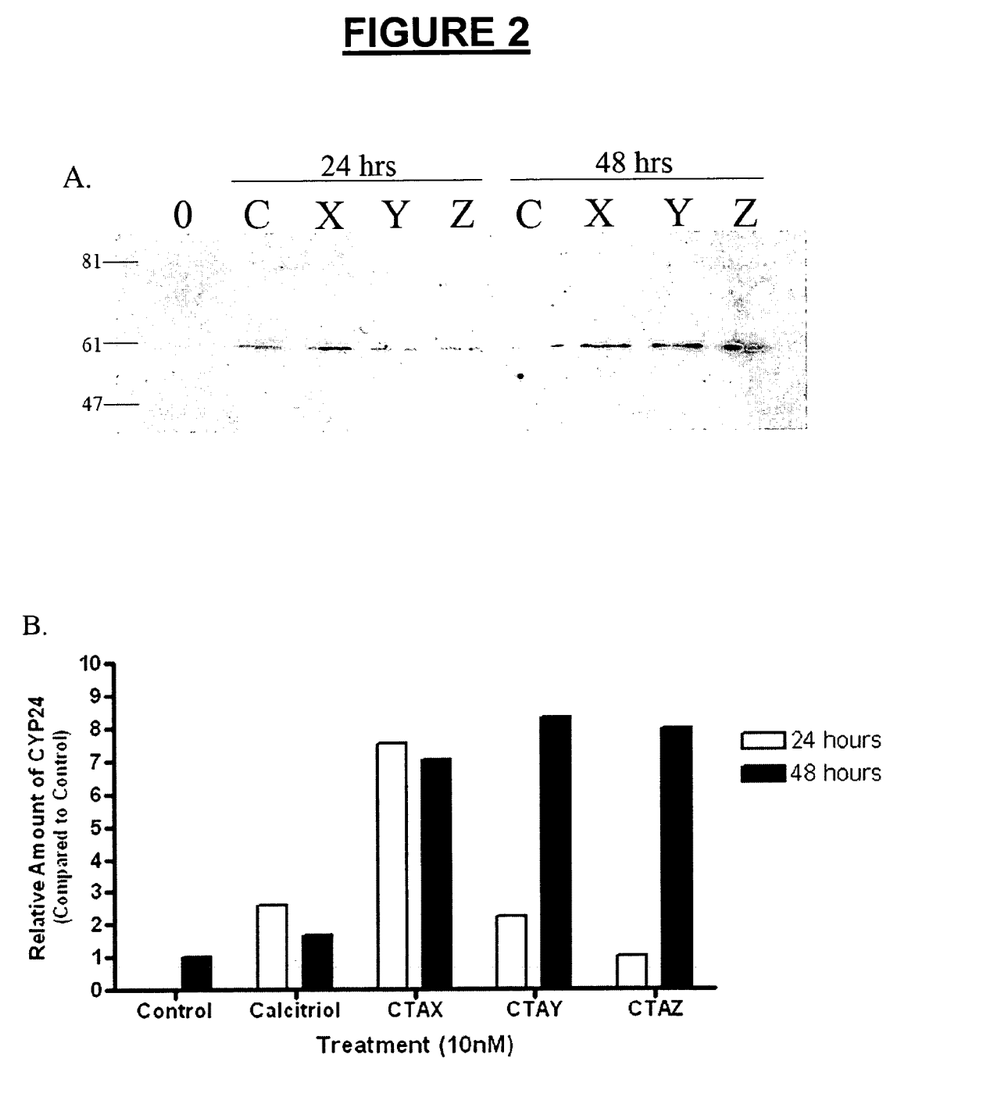
FIG. 2A is a Western Blot illustrating the effect of CYP24 protein expression in HEK cells treated with CYP24 inhibitors.
FIG. 2B is a bar graph illustrating the densometric analysis of CYP24 Western Blot on HEK cell lysates.

As shown in FIG. 2, Calcitriol weakly induces the production of CYP24 protein in HEK cells after 24 and 48 hours. In comparison, CYP24 inhibitor CTAX incubation with HEK cells resulted in greater induction of CYP24 protein at 24 and 48 hours. CYP24 inhibitor CTAY weakly induces CYP24 protein after 24 hours, but strongly induces CYP24 protein after 48 hours. CYP24 inhibitor CTAZ has no effect on CYP24 protein at 24 hours, but at 48 hours, it strongly induces CYP24 protein in HEK cells.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. An isolated monoclonal antibody specific to CYP24 wherein the antibody binds specifically to the CYP24 epitope C-QRLEIKPWKAYRDYRKE-NH$_2$ (SEQ. ID. NO. 2).

2. A hybridoma cell line that can produce a monoclonal antibody of claim 1.

3. The monoclonal antibody of claim 1 that is labeled to enable detection of bound and unbound CYP24.

* * * * *

UNITED STATES PATENT AND TRADEMARK OFFICE
CERTIFICATE OF CORRECTION

PATENT NO. : 7,427,670 B2  Page 1 of 1
APPLICATION NO. : 11/013435
DATED : September 23, 2008
INVENTOR(S) : Samuel S. Chuang et al.

It is certified that error appears in the above-identified patent and that said Letters Patent is hereby corrected as shown below:

On the Cover Page:

Item (73), "Markham, Ontario" should be -- Markham (CA) --.

Signed and Sealed this

Fifth Day of January, 2010

David J. Kappos
*Director of the United States Patent and Trademark Office*